US00PP09659P

United States Patent [19]

Nies

[11] Patent Number: Plant 9,659

[45] Date of Patent: Oct. 15, 1996

[54] CHERRY TREE 'GIANT RED'

[76] Inventor: Marvin L. Nies, 9296 E. Kettleman, Lodi, Calif. 95240

[21] Appl. No.: 515,923

[22] Filed: Aug. 17, 1995

[51] Int. Cl.[6] ..... A01H 5/00

[52] U.S. Cl. ..... Plt./37

[58] Field of Search ..... Plt./37

[56] References Cited

U.S. PATENT DOCUMENTS

| | | | |
|---|---|---|---|
| P.P. 4,431 | 6/1979 | Nies | Plt./37 |
| P.P. 4,436 | 10/1979 | Nies | Plt./37 |
| P.P. 9,368 | 11/1995 | Nies | Plt./37 |

*Primary Examiner*—James R. Feyrer

[57] ABSTRACT

Hardy tree of medium size and vigor; from 'Large Red'× 'Ruby'. Less open and spreading than 'Large Red', more open than 'Ruby'. Self-shapes to rounded figure and moderate density, from open, leggy specimen. Scaffolds have strong, wide angles; secondary branching pendulous. Fruiting precocious, regular, and on spurs spaced about 6 cm; each having 5–6 fertile buds. May overbear on warm, dry years; sets well in wet, rainy weather during pollination, as in 1995. Mature leaves on 1-year wood are large, ovate, acuminate, acutely pointed; margins medium coarsely crenate; spur leaves are smaller, less crenate, more serrate, like those of 'Large Red'. Blooms 6 days after 'Early Red', 2 days after 'Ruby', 4 days before 'Garnet' and 'Large Red', 9 days before 'Bing' in Lodi. Fruit on May 15, 1994 following 'Early Red' by 10 days, 'Ruby' by 3, but 3 days before 'Garnet', 9 days before 'Bing'. Fruit is unformly very very large with normal crop load; fruit stems are medium long when on Mahaleb stock. Fruiting uniformly on branches throughout tree; of uncommonly uniform ripening. Flesh is firm, meaty at picking ripe, slightly less firm than standards 'Garnet' and 'Bing'. Eating quality is exceptionally fine with high soluble solids, low/moderate acid, very agreeable sugar to acid ratio and semi-free stone. Flesh and juice are light red when skin attains solid light red; darkens with progressive ripeness.

1 Drawing Sheet

FIELD OF INVENTION

The present variety of cherry tree has been denominated varietally as "Giant Red," however, the fruit produced will be marketed under the Trade Mark (™) "Giant Ruby." This variety is the outgrowth of a plant breeding program which has been conducted by me on a continuous basis since 1957 in my Experimental Orchard near Lodi, County of San Joaquin, Calif. One part of the program has been to develop new and distinct varieties of cherries to be grown commercially in the warmer, lower humidity, lower chilling, earlier production areas, with the tree to have adequate heat tolerance, fruit that is free of sutures, spurs and doubles in hotter climates, holding on the tree well without ripening too quickly, with no spurs and doubles, fruit that is very very large, with very firm flesh, adequate thick skin, early ripening, possessing outstanding flavor with high soluble solids, pleasing sugar/acid ratio, non-astringent, non-browning skin and flesh and with adequate disease and insect resistance. The present variety has achieved these objectives with the exception of a tendency to develop, on a small percentage of fruit, a wide, rounded cleavage the sides of which taper obliquely to a point at varying distances towards the apex. The fruit has a tendency to crack in wet weather as the fruit matures from pink color to full dark red color, with the amount of cracking as compared with many of the other commercial varieties being comparable at the same stage of ripening. Very very large size, uniform ripening, uniform maturity at harvest, firmness of the fruit and the excellent dessert qualities of the fruit, make this selection an excellent candidate for the ultimate commercialization of the variety. The present cherry tree is embraced by Subclass 37, Plants, of the Plant Patent Office, MANUAL OF CLASSIFICATION.

PRIOR VARIETIES

Among the existing varieties of cherry trees which are known to me are those mentioned herein; to-wit Prunus mahaleb rootstock (unpatented), Colt rootstock (U.S. Plant Pat. No. 4,059), Ruby (U.S. Plant Pat. No. 4,436), Garnet (U.S. Plant Pat. No. 4,431), Bing (unpatented), Large Red (Patent Pending) the fruit of which will be sold under the trademark "Lodi", Early Red, U.S. Plant Pat. No. 9,368, the fruit of which will be marketed under the trademark "Early Garnet".

ORIGIN OF THE VARIETY

The present variety, denominated varietally as "Giant Red," relates to a distinct variety of cherry tree originated by me, the fruit of which was first observed by me in 1982 in the seedling block of my experimental orchard in a cultivated area at the Marvin L Nies ranch near Lodi, County of San Joaquin, Calif., and was initiated in 1976 by crossing the selected seed parent Large Red with the selected pollen parent Ruby, which resulted in seeds from the seed parent, which when germinated and grown, produced some seedlings, one of which was the present variety; the location of which in the seedling block was recorded in my Breeding Records as Seedling T 8-22-4, and which when grown to maturity, evidenced novel and distinctive characteristics, and I therefore selected it for asexual reproductions preparatory to patenting and ultimate commercial growing thereof.

ASEXUAL REPRODUCTION OF THE VARIETY

Subsequent to the origination of the present variety of cherry tree I asexually reproduced the selection on Prunus mahaleb rootstock and at a later date on Colt rootstock in my experimental orchard near Lodi, County of San Joaquin, Calif., by budding and grafting, and such reproduction of plant and fruit characteristics were true to the original plant at maturity in all respects.

SUMMARY OF VARIETY

My first observation of the fruit of this variety was made in 1982 in my experimental orchard seedling block in Lodi, San Joaquin County, Calif. What set the present variety apart from the sister seedlings was primarily the shiny dark red color, very very large size of the fruit, outstanding flavor, high soluble solids, moderate acidity with excellent sugar/acid ratio and fruit that was very even in maturity when picking ripe. The present variety had medium vigor, was fairly open, a semi-pendulous tree of ideal form, being intermediate in habit between Large Red and Ruby, precocious in cropping, flesh of the fruit quite firm and meaty (slightly softer than Bing, the industry standard for firmness), stone semi-free to free, fairly long fruit stems that were not as long as those of Large Red but longer than those of Ruby, light red flesh and juice when the skin was light red in color, dark red flesh and juice when fully mature, Susceptibility to cracking in wet weather, slightly greater than with Garnet and Ruby. As the tree becomes more mature it has a natural tendency to shape itself and remains quite open, having fairly wide angled pendulous lateral branches originating from the upright branches. The younger trees require little if any pruning, however, with older trees pruning may be necessary to limit the crop level when they begin to bear too heavily. The present variety is generally picking ripe ten (10) days after early Red, three (3) days after Ruby, two (2) days before Garnet, five (5) days before Large Red, and eight (8) days before Bing. Since thinning of fruit in cherries after bloom does not increase fruit size due to the short Fruit Development Period (FDP), "what you see is what you get". Conseqently growers traditionally attempt to control the crop level mostly by pruning to remove some of the fruiting wood. Under normal conditions, the present variety produces very consistent large crops, making it possible to make ball park predictions as to the amount of pruning that must be done to obtain the crop load desired. Crops that are too heavy result in soft fruit, low in soluble solids, diminished flavor, more susceptibility to fruit damage (pitting) from the packing operation, the end result being a product that is of poor quality and that has very poor shelf life on the retail level with the inevitable demand by the trade for price adjustments. Limiting the crop to normal or slightly below normal levels by pruning can result in excellent quality, firm, high soluble solids and flavorful fruit. One of the major cost problems in cherry production, with Bing, the present major production variety a prime example, is uneven ripening, sutures, spurs and doubles. All of these contribute to a high percentage of cull fruit especially in low chilling years which cause the tree to produce late straggle bloom and very hot weather in the summer which causes the three to produce suture, spurs and doubles. The FDP for any selected individual fruit on a tree is quite consistent from year to year. Late straggle bloom creates uneven maturity at harvest-time forcing the grower to color pick. Color picking is a high cost, slow, tedious process in which all of the fruit that is solid light red to black in color is picked at one time, however, if no enough green fruit is left behind for a later picking to be economic, all the fruit on the tree (stripping) is picked at one time resulting in large amounts of green cull (brine) fruit. A wide spread in maturity of the picked fruit when processed in the packing house results in a checkerboard appearing box (fruit of various shades of red) which is discounted by the trade in the marketplace. Significant losses from cull fruit (doubles, spurs and green fruit) that is not marketed, may reduce the gross sales by up to forty percent (40%). All of the above factors contribute to a very much high cost per packed box than would be incurred with the present variety. The losses are not only confined to the additional cost of harvesting and handling of the fruit eliminated but also the in the loss of the fruit that is not marketed. The present variety overcomes the above enumerated problems, with the end result being a higher return for the fruit. In summary, the favorable qualities of the present variety, with its desirable tree habit and shape, very very large fruit of uniform size, even maturity when picking ripe, heavy consistent cropping that makes crop control by pruning a more reliable cultural practice, outstanding flavor, high soluble solids, moderate acidity, with no spurs and doubles, make this variety desirable not only from a production standpoint but will make it successful in the market place when its true qualities become apparent.

DRAWING

The accompanying photograph exhibits clusters of whole fruits positioned to display the form of the fruit, skin color, stem length on a representative branch with buds, spurs and leaves, with two (2) detached fruits that were sectioned — one (1) cut longitudinally showing the ventral half, with the dorsal side of the stone showing, the dorsal half of the fruit showing the stone cavity and a transverse section showing the basal (½), illustrating the color and texture of the flesh and with the apical end of the stone showing.

POMOLOGICAL CHARACTERISTICS

The botanical details of this new and distinct variety of cherry tree with color definitions (except those in common color terms) referenced to the Wilson Colour Chart I and II, published by The British Colour Council-Horticultural Color Chart (1938) are as follows:

Tree:

*Size.*—Medium on Prunus mahaleb and Colt rootstocks.

*Vigor.*—Good.

*Growth.*—Open, Spreading-quite pendulous.

*Density.*—Open.

*Form.*—Bushy — Rounded.

*Hardiness.*—Hardy.

*Production.*—Even crop levels from year to year. Tendency to overcrop if not pruned. Even distribution of the fruit throughout the tree. Even maturity. Uniform size.

Trunk:

*Size.*—Medium.

*Texture.*—Medium.

Branches:

*Size.*—Medium.

*Texture.*—Medium.

*Color.*—Dark brown on younger wood — dull grayish brown on older wood.

*Lenticels.*—Pronounced. Medium to large on two year wood — light brown.

*Number.*—Some. Not too numerous.

Leaves:

*Size.*—First years mature growth — Large — average length (25 leaves) 14.8 cm. Average width (25 leaves) 6.5 cm. Ratio: width/length 0.44. Leaves emanating from spurs on two year wood — generally small to medium in blade size — very variable in size.

*Veination.*—Large vein centrally oriented from base of blade to apex. Lateral veins oblique towards apex of blade — extending from main central vein forming a looped configuration near margin. No pigmentation.

*Form.*—Ovate. Acuminate. Acutely pointed.

*Thickness.*—Medium.

*Color.*—Top of leaf — dark green. Bottom of leaf — light green. Leaf margins roll very markedly upward in mid-season on scaffold branches, exposing the lighter green, dull underside of the blade, creating an impression that the tree is water stresed, this general appearance being almost identical with that of Ruby, the pollen parent, The general appearance of the three with its rolled leaves are very obvious and is an aid in the identification of the present variety.

*Texture.*—Smooth.

*Margin.*—Crenate.

*Petiole.*—On current years mature shoots — quite long — 4 cm to 5 cm. Light red on upper surface of stalk. No pigment on small leaves on spurs of second years wood. Ratio: Petiole length/length of blade — 0.24 (Average 25 leaves).

*Glands.*—Located on petiole near blade. Glabrous. Reniform. Color — very light red tinge on upper surface — sharply compressed. Located short distance from blade. Number: On the petioles of one year vigorous upright shoots with large blades — predominately two (2) — but sometimes up to four (4) — offset opposite — the size being quite large. On smaller leaves — size is small — one (1) — occasionally none — sometimes with an inconspicuous gland on the blade near petiole. On two (2 ) year shoots that have smaller leaf blades — the smaller leaves are generally eglandular. Sometimes on the large blades — occasionally one (1) — very occasionally a very inconspicuous gland on the petiole or attached to the blade near the petiole.

*Stipules.*—Two (2) — one (1) on each side of petiole on young leaves.

Flower buds:

*Hardiness.*—Hardy.

*Size.*—Medium.

*Length.*—Medium.

*Form.*—Conic-plump.

Flowers:

*Date of bloom.*—Mar. 12, 1994.

*Petals.*—Number: Five (5). Color — pure white. Size — medium large — length 15.0 mm. Width — 16.0–17.0 mm. Color — pure white. Striated-shell like appearance. At midpoint — overlapping ¼th of the width over next petal. Some slightly notched at apex.

*Filament length.*—5.0 to 13.0 mm.

*No. of filaments.*—Almost always twenty five (25) to twenty eight (28).

*Stigma length.*—1.4 cm.

*Hypanthium.*—Medium. Five (5) petals. Five (5) sepals. No pigmentation. Strongly reflexed on mature flowers. Very slight reddish tinge on hypanthium.

*Blooming period.*—Compact — no staggle bloom.

*No. of flowers per bud.*—Quite consistently four (4).

*Flower stalk.*—Length 3.9 cm. Color; Veronese green (660/2).

Fruit:

*Maturity when described.*—Eating ripe — May 14, 1994.

*Date of first picking.*—May 14, 1994. All fruit picked at one time.

*Size.*—Very uniform. Large. Average width — longitudinal plane — 30 mm. Suture plane — 23.6 mm. maximum width observed — 34 mm. Average size 75/64" (9Row) — 29.8 mm.

*Form.*—Globose. Uniform. Symmetrical in transverse and longitudinal planes — Asymmetrical in suture plane. Very large, prominent shoulders at base. Rounded on ventral surface — strongly rounded on dorsal surface. Longitudinal plane — Sides from mid-point towards apex-rounded-oblique. Some fruit has a strong cleavage on the suture line from base to near midpoint — many times extending to apex — slightly depressed at pistil point.

*Suture.*—Some. Small percentage of the fruit in hotter climates.

*Spurs and doubles.*—None.

*Ventral surface.*—Slightly rounded from base to apex. Slightly compressed.

*Dorsal surface.*—Strongly rounded. Wide — shallow — slightly compressed groove midpoint — from base to apex.

*Stem cavity.*—Flaring — Wide. Circular. Elongated in the suture plane. Very pronounced. Depth of cavity from top of shoulder of the base to bottom of cavity — 4 mm — (fruit size — 32.2 mm — longitudinal plane).

*Color.*—Dark red when fully mature with uniform color over the total surface — Currant Red (821/2).

Base: Shoulders very prominent — very strongly rounded.

*Stem cavity.*—Large — deep — very pronounced.

*Apex.*—Rounded.

*Pistil point.*—Apical. An inconspicuous brown abscission point.

*Ripening span.*—Very even ripening. One picking.

Skin:

*Thickness.*—Medium.

*Texture.*—Medium.

*Tenacity.*—Tenacious to flesh.

*Tendency to crack.*—None in dry weather. Susceptible in wet weather — generally the same as other commercial varieties.

*Color.*—Mature fruit-picking ripe — Currant Red (8/21).

*Down.*—Wanting.

*Surface.*—Shiny-glassy appearance.

Flesh:

*Color.*—Fully mature fruit — Red (Currant Red 821/2).

*Surface of pit cavity.*—Red (Currant Red 8/21).

*Amygdalin.*—Wanting.

*Texture.*—Firm — fine — meaty.

*Aroma.*—Wanting.

*Fibres.*—Few — very fine.

*Ripens.*—Very evenly.

*Flavor.*—Exceptional at fully maturity.

*Eating quality.*—The best. High soluble solids. Low to moderate acidity. Excellent sugar/acid ratio.

*Tendency to crack.*—None in dry weather. Equal to other commercial varieties in wet weather.

Stone:

*Type.*—Semi-free to free.

*Size.*—Medium large. Average length — 10 mm. Average width — 7.0 mm. Average breath — 8.0 mm.

*Form.*—Globose.

*Base.*—Slightly oblique.

*Hilum.*—Long. Narrow. Oblong.

*Apex.*—Pointed.

*Sides.*—Equal. Symmetrical.

*Surface.*—Smooth from dorsal edge to flattened, ridged ventral edge.

*Ridges.*—Jagged.

*Ventral edge.*—Width — 4 mm at midpoint of stone. Edge prominently rounded from base to apex. Three (3) prominent ridges from hilum to apex — one very prominent — thick — central ridge that is winged — extending away from the main contour of the stone two (2) mm. Two (2) thinner and smaller lateral ridges form a narrow-pointed elliptical configuration (point near the apex) — curving at midpoint away from the central ridge 2 mm.

*Dorsal edge.*—Narrow — an almost inconspicuous ridge.

*Color.*—Egyptian Buff (407/1).

*Form.*—Oval. Flattened on ventral side. Strongly rounded on dorsal side from hilum to apex — oblique to apex.

*Taste.*—Seed very bitter.

*Viability.*—Very low.

*Amygdalin.*—Abundant.

Use: Market. Dessert. Shipping.

Keeping quality: Excellent.

Resistant to insects and diseases: No unusual susceptibilities noted.

Shipping quality: Good — both local and long distance.

Variance in botanical details: Although the new variety of cherry possesses the described characteristics under the ecological conditions at Lodi, Calif., in the Northern part of the San Joaquin Valley, it is to be expected some variations in some of these pomological characteristics may occur when grown in areas with different climatic conditions, different soil types,

I claim:

1. A new and distinct variety of cherry tree, substantially as illustrated and described, being of medium vigor, lateral branches with relatively wide, flat angles with the axis of the main branches, pendulous smaller branches, tree habit open, spreading, self shaping, and like Large Red requiring almost no pruning when young, some pruning for crop control when the more mature trees begin to bear too heavily, the fruit being very very large and quite uniform in size, slightly larger size than Large Red, with even distribution the length of the branches and throughout the tree, the fruit being moderately rounded on the ventral side, strongly rounded on the dorsal side with a fairly wide, very shallow compressed groove from base to apex, symmetrical in the transverse and longitudinal planes but asymmetrical in the suture plane, having high soluble solids with moderate acidity, attractive shiny dark red color when fully mature, having a fairly long fruit stem which is shorter than the fruit stem of Large Red, of medium thickness, a fruit that is physically easy to remove from the tree by pickers, and when compared with Large Red, which the present variety most closely resembles, equally precocious, heavier cropping, Large Red tending to produce more normal, lignter crops from year to year, fruit that is of equal firmness, no tendency to brown on the skin — which is a problem with Large Red, even red color of the skin just before ripening as opposed to the speckled appearance of Large Red, slightly darker skin and flesh color at maturity, holds equally well on the tree without a tendency to turn black, larger in size with equivalent crop levels, picking ripe five (5) days earlier, having a slightly lower chilling requirement, cracking slightly more in wet weather, with a few sutures, but no spurs or doubles in the hotter Central Valley of Northern California.

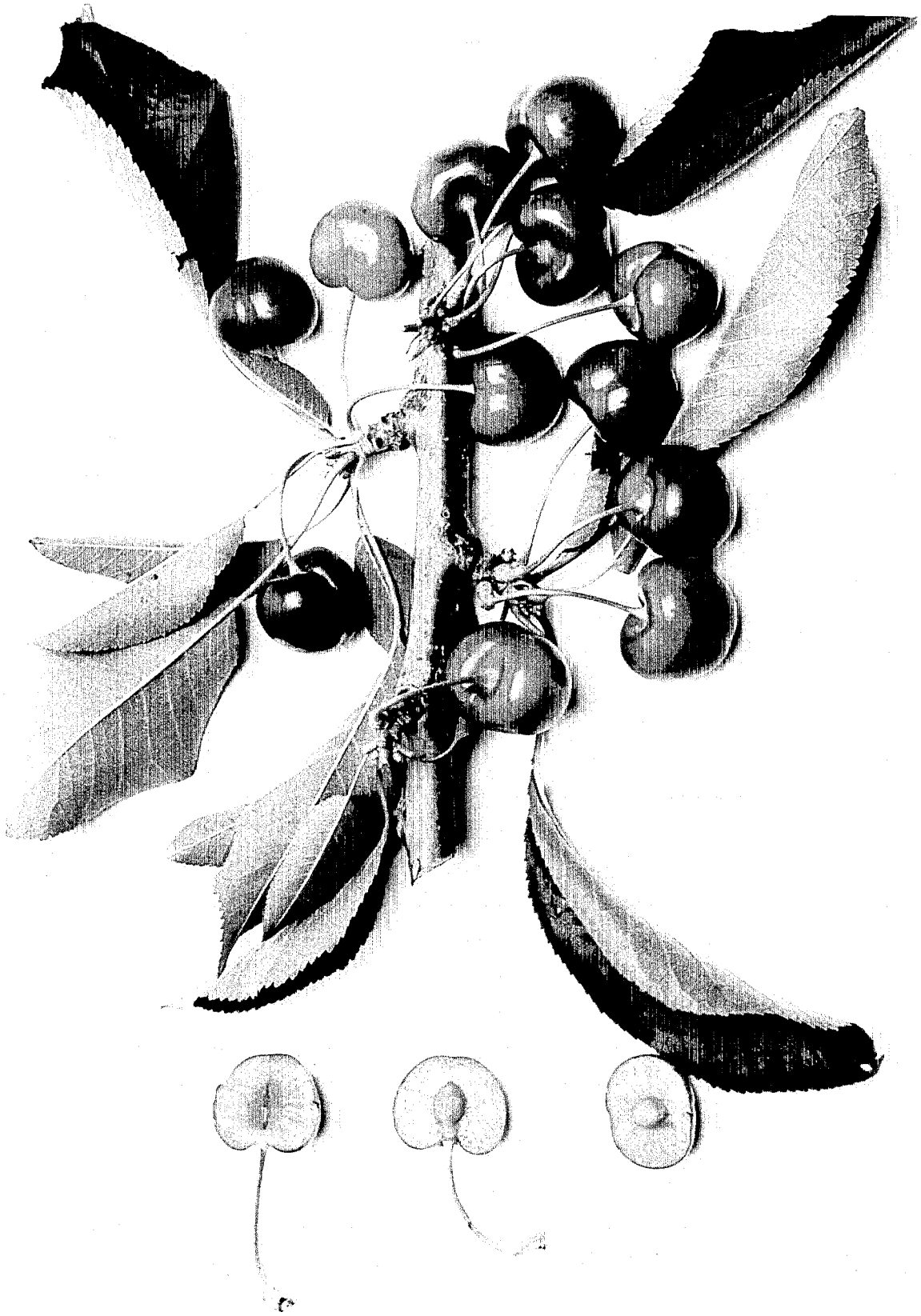

* * * * *